United States Patent
Morita et al.

(10) Patent No.: US 7,886,398 B2
(45) Date of Patent: Feb. 15, 2011

(54) ORAL CAVITY CLEANING TOOL

(75) Inventors: Toyoko Morita, Tokyo (JP); Toshiaki Kobayashi, Tokyo (JP); Takao Kato, Tokyo (JP)

(73) Assignee: Lion Corporation, Tokyo (JP)

( * ) Notice: Subject to any disclaimer, the term of this patent is extended or adjusted under 35 U.S.C. 154(b) by 943 days.

(21) Appl. No.: 11/243,457

(22) Filed: Oct. 3, 2005

(65) Prior Publication Data

US 2006/0070195 A1    Apr. 6, 2006

(30) Foreign Application Priority Data

Oct. 5, 2004    (JP) .............................. 2004-292467

(51) Int. Cl.
    *A46B 9/04*    (2006.01)
(52) U.S. Cl. ........................................ 15/167.1; 433/32
(58) Field of Classification Search .................. 15/105, 15/106, 167.1, 207.2; 433/29, 32, 141; 604/20
    See application file for complete search history.

(56) References Cited

U.S. PATENT DOCUMENTS

| | | | | |
|---|---|---|---|---|
| 3,478,741 A | * | 11/1969 | Simor | 604/20 |
| 3,520,297 A | * | 7/1970 | Bechtold | 604/20 |
| 3,645,260 A | * | 2/1972 | Cinotti et al. | 604/20 |
| 4,691,718 A | * | 9/1987 | Sakuma et al. | 433/32 |
| 6,314,605 B1 | * | 11/2001 | Solanki et al. | 15/167.1 |

FOREIGN PATENT DOCUMENTS

| | | |
|---|---|---|
| DE | 19605845 A1 * | 8/1997 |
| EP | 0357852 A1 * | 3/1990 |
| JP | S54-91969 | 6/1979 |
| JP | A-02-088002 | 3/1990 |
| JP | 2-239808 A | 9/1990 |
| JP | 5-76417 A | 3/1993 |
| JP | 5-154480 A | 6/1993 |
| JP | 10-042962 | 2/1998 |
| JP | 11-151256 A | 6/1999 |
| JP | 2001-190336 | 7/2001 |
| JP | 2001-309820 A | 11/2001 |
| JP | 2004-25185 A | 1/2004 |
| JP | 3493359 B1 | 10/2004 |

OTHER PUBLICATIONS

Computer generated English translation of DE 19605845 A1, Aug. 1997.*
Japanese Office Action mailed Jul. 20, 2010 for the counterpart Japanese application No. 2004-292467.

* cited by examiner

*Primary Examiner*—Laura C Guidotti
(74) *Attorney, Agent, or Firm*—Leason Ellis LLP.

(57) ABSTRACT

An oral cavity cleaning tool for the purpose of sterilization of the inside of oral cavity is provided that carries out efficient sterilization by using effective chlorine that is obtained through electrolysis. The oral cavity cleaning tool comprises a block handle, a head section extending from the block handle, a pair of electrodes provided on the head section and a power source that supplies electric current to the pair of electrodes, wherein the electrodes are put into contact with an oral fluid that contains chloride ions thereby to cause electric current to flow between the electrodes, so that the chloride ions are transformed into effective chlorine.

4 Claims, 4 Drawing Sheets

ELECTRODE LAYOUT (1)

FIG.4

ELECTRODE LAYOUT (2)

FIG.5

ELECTRODE LAYOUT (3)

FIG.6

ELECTRODE LAYOUT (4)

FIG.7

ELECTRODE LAYOUT (5)

FIG.8

ELECTRODE LAYOUT (6) (PLURALITY OF ELECTRODE)

FIG.9

ELECTRODE LAYOUT (7) (PLURALITY OF ELECTRODE)

FIG.10

ELECTRODE LAYOUT (8) (ELECTRICALLY CONDUCTIVE BRISTLES)

FIG.11

ELECTRODE LAYOUT (9) (ELECTRICALLY CONDUCTIVE BRISTLES)

FIG.12

WIRING FOR ELECTRICALLY CONDUCTIVE BRISTLES (ENLARGEMENT OF A HEAD SECTION)

ELECTRODE BY ELECTRICALLY CONDUCTIVE BRISTLES (ANODE)
WIRING FOR AN ELECTRODE (ANODE)
WIRING FOR AN ELECTRODE (CATHODE)
ELECTRODE BY ELECTRICALLY CONDUCTIVE BRISTLES (CATHODE)

FIG.13

ELECTRODE LAYOUT
(USE ELECTRICALLY CONDUCTIVE BRISTLES AND METALLIC ELECTRODE TOGETHER)

ELECTRODE BY ELECTRICALLY CONDUCTIVE BRISTLES (ANODE)
METALLIC ELECTRODE (ANODE)
METALLIC ELECTRODE (CATHODE)
ELECTRODE BY ELECTRICALLY CONDUCTIVE BRISTLES (CATHODE)

ORAL CAVITY CLEANING TOOL

BACKGROUND OF THE INVENTION

1. Field of the Invention

The present invention relates to an oral cavity cleaning tool and, more particularly, to an oral cavity cleaning tool having electrodes mounted on a head section thereof with electric power supplied to the electrodes so as to turn chloride ions existing in an oral cavity into effective chlorine that carries out sterilization.

Priority is claimed on Japanese Patent Applications No. 2004-292467, filed Oct. 5, 2004, the content of which are incorporated herein by reference.

2. Description of the Related Art

Toothbrushes that have sterilization and dental plaque removing functions include one that has bristles treated with an antibacterial agent. There are, for example, one that has bristles treated with an antibacterial agent such as cetylpyridium chloride applied to the surface thereof (Japanese Unexamined Patent Application, First Publication No. Hei 2-239808), one that includes an antibacterial agent such as zinc oxide and one that has sterilization function incorporated in tuft holes (Japanese Unexamined Patent Application, First Publication No. Hei 5-76417), all of which are intended to provide sterilization or anti-bacterial function addressed only to bacteria deposited on the bristles.

Another example of toothbrush that has sterilization and dental plaque removing functions is one that is called the ionization toothbrush (Japanese Unexamined Patent Application, First Publication No. 2001-309820). The ionization toothbrush comprises a head section having brushing bristles planted therein and a block handle that incorporates a commercially available battery. An electrically conductive plate connected to one of electrodes of the battery is disposed in a part of the surface of the block handle, and an electrically conductive rod connected to the other electrode of the battery is disposed in the head section. Thus an electric circuit is formed from one of the electrodes of the battery incorporated in the block handle of the toothbrush, the terminal disposed on the surface of the block handle, a hand, corresponding arm, neck, oral tissue, teeth and gum of the user, the brushing bristles, an electrically conductive member and returning to the other electrode of the battery. Electric current in a section of this circuit between the brushing bristles and the tooth surface is carried by calcium ions included in the saliva. Accordingly, electrostatic crosslinkage that bonds the tooth surface and dental plaque is destroyed by the calcium ions, thus making the dental plaque loose so that brushing of the teeth has higher cleaning effect.

There have been the following methods of sterilization based on electrochemical process and electrolysis.

An example of electrochemical sterilization is disclosed in Japanese Unexamined Patent Application, First Publication No. Hei 5-154480, although it does not have the configuration of toothbrush, wherein an operation electrode is provided in an electrochemical sterilization apparatus, with a potential of 0.6 V vs SCE or higher applied to the operation electrode thereby to carry out sterilization.

An electrolytic water manufacturing apparatus for electrolytic sterilization comprising a cathode, an anode and a partition wall that separates the former ones is known from Japanese Unexamined Patent Application, First Publication No. 2004-25185, wherein electrolytic water is produced at the anode and alkaline water is produced at the cathode. In this apparatus, salt water prepared from table salt or the like is put into an electrolytic tank so that water is electrolyzed to produce acidic water and alkaline water at the cathode and the anode, respectively, that are used as required.

Japanese Unexamined Patent Application, First Publication No. Hei 11-151256 discloses a false teeth cleaning apparatus that produces hydrogen gas and hypochlorous acid used for sterilization based on electrolysis.

Japanese Patent No. 3493359 discloses an ion migration treatment apparatus that carries out sterilization by means of ion migration. An ailing portion of human body is infiltrated with a liquid medicine by means of an ion migration apparatus by supplying an electric current of 40 μA or less for several seconds. Current is limited to 40 μA so as to treat the ailing portion without causing damage (side effect) to the living tissue due to the medicine.

A toothbrush is intended basically to physically remove food particles and dental plaque, not for the purpose of sterilization. In the meantime, in view of the increasing public awareness about cleaner oral cavity, it would be very useful to add sterilization function to a toothbrush. In practice, however, it is not possible to carry out sterilization inside of oral cavity by means of a single tool such as toothbrush, unless an antibacterial agent is used together. The toothbrushes described in Japanese Unexamined Patent Application, First Publication No. Hei 2-239808 and Japanese Unexamined Patent Application, First Publication No. Hei 5-76417 are both intended to sterilize or reduce bacteria deposited on the toothbrush itself, and are not intended to carry out sterilization of bacteria inside of the oral cavity. The ionization toothbrush described in Japanese Unexamined Patent Application, First Publication No. 2001-309820 is intended to increase the cleaning effect of tooth brushing by making dental plaque loose and easy to remove, not for sterilization of bacteria inside of the oral cavity.

The electrolytic water manufacturing apparatus described in Japanese Unexamined Patent Application, First Publication No. 2004-25185 electrolyzes water or an electrolyte to produce acidic water and alkaline water that have sterilizing power. This apparatus has such a drawback that it requires two electrolytic cells and results in a large and complex apparatus. It also has such a problem that it is difficult to achieve sterilization effect unless the acidic water produced in the electrolytic cell is used immediately, as it is known that effective chlorine decays with time.

The false teeth cleaning apparatus described in Japanese Unexamined Patent Application, First Publication No. Hei 11-151256 is not intended for use in the oral cavity, but stores aqueous solution after the electrolysis in a tank, similarly to the electrolyzed water manufacturing apparatus. Since it is not intended for use in the oral cavity, it has the problem that effective chlorine decays with time, similarly to Japanese Unexamined Patent Application, First Publication No. 2004-25185. Also because it is not intended for use in the oral cavity, it is not subject to any limitations with regard to the voltage level, size of the apparatus, concentration of effective chlorine, etc. Therefore, it is difficult to apply the technology described in Japanese Unexamined Patent Application, First Publication No. Hei 11-151256 to such applications as oral cavity cleaning tool that makes direct contact with a human body.

Under these circumstances, the present invention has been completed and an object thereof is to provide an oral cavity cleaning tool that carries out sterilization inside of the oral cavity efficiently by using effective chlorine obtained by electrolysis, without using a sterilizer, and an oral cavity cleaning tool that employs a simple apparatus, not a large apparatus, so that it can be used in the oral cavity without using a solution produced by electrolysis outside the oral cavity to counter the degradation of effective chlorine.

SUMMARY OF THE INVENTION

The object described above is achieved by the present invention by employing the following constitution.

The oral cavity cleaning tool of the present invention comprises a block handle, a head section extending from the block handle, a pair of electrodes provided on the head section and a power source that supplies electric current to the pair of electrodes, wherein the pair of electrodes are put into contact with an oral fluid that includes chloride ions thereby to cause electric current to flow between the electrodes, so that the chloride ions are transformed into effective chlorine.

According to the constitution described above, sterilization inside of the oral cavity can be accomplished by the effective chlorine that is generated. In particular, as the pair of electrodes provided on the oral cavity cleaning tool of the present invention is put into the oral cavity so as to make contact with the oral fluid that includes chloride ions, the oral fluid can be electrolyzed thereby to turn the chloride ions into effective chlorine. Thus sterilization inside of the oral cavity can be done without using a chemical that has antibacterial power.

Since the effective chlorine is generated in the oral cavity, the effective chlorine that has been generated can be immediately used for sterilization. Thus the effective chlorine can be used efficiently without the need to give consideration to the degradation of chlorine with time.

Moreover, the oral cavity cleaning tool of the present invention is simple in construction and can be used easily, with no need of a large and complicated structure such as the electrolysis water manufacturing apparatus of the prior art.

The oral fluid mentioned in the present invention means a solution that includes $Cl^-$, such as saliva, the fluid filling the oral cavity during teeth brushing, mouth rinsing liquid, gargling liquid, mouth spray, sports drink (AQUARIUS®, POCARI SWEAT®, etc.) and the like.

The effective chlorine mentioned in the present invention includes chlorine gas ($Cl_2$), hypochlorous acid (HClO) and hypochlorous acid ion ($ClO^-$), which are forms of chlorine having sterilizing power.

The oral cavity cleaning tool of the present invention is the abovementioned oral cavity cleaning tool, that generates effective chlorine of a concentration in a range from 2 ppm to 100 ppm when the oral fluid is physiological saline.

The concentration of effective chlorine is more preferably in a range from 5 ppm to 60 ppm.

When the concentration of effective chlorine is lower than 2 ppm, sufficient effect of sterilization inside of the oral cavity cannot be achieved as the water quality standard for city water is specified to be not higher than 1 ppm. While sterilization effect is achieved when the concentration of effective chlorine is 2 ppm or higher, higher effect is obtained when it is 5 ppm or higher. When the concentration of effective chlorine is 70 ppm or higher, odor of chlorine is felt a little. Thus it is preferably 60 ppm or lower.

With the constitution described above, since the concentration of effective chlorine is kept within the range described above, efficient sterilization can be achieved without any harm to the human body when used in the oral cavity.

The oral cavity cleaning tool of the present invention is the abovementioned oral cavity cleaning tool, that generates effective chlorine at a rate in a range from 0.5 ppm per minute to 35 ppm per minute when the oral fluid is physiological saline.

With the constitution described above, since the rate of generating effective chlorine is kept within the range described above, efficient sterilization can be achieved with the concentration of effective chlorine in the oral cavity maintained substantially constant when used in the oral cavity.

The oral cavity cleaning tool according to the present invention, because of the compact construction and low operating voltage that ensures safety, can be easily used so as to achieve tooth brushing effect while being held in a hand. The oral cavity cleaning tool according to the present invention can be applied to a toothbrush or the like, making it possible to spread the effective chlorine that is locally generated throughout the oral cavity by the brushing action, thereby achieving efficient sterilization inside of the oral cavity.

DETAILED DESCRIPTION OF THE PREFERRED EMBODIMENTS

Figure 1:
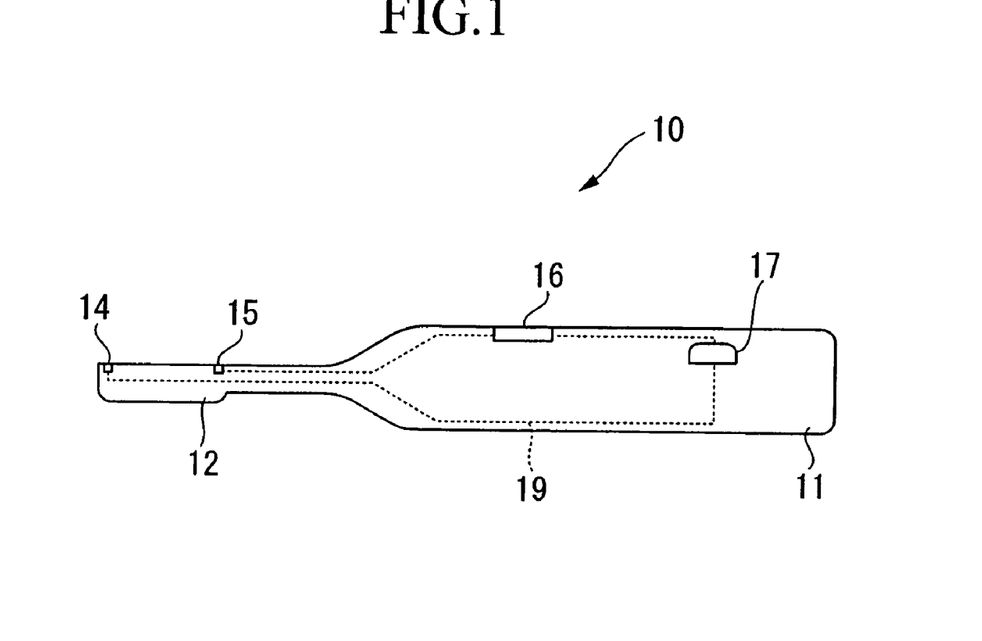
FIG. 1 illustrates the oral cavity cleaning tool of the present invention.

The present invention will now be described by way of embodiments with reference to the accompanying drawings. FIG. 1 schematically shows the oral cavity cleaning tool of the present invention. The oral cavity cleaning tool 10 comprises a block handle 11 and a head section 12 that extends from the block handle 11. The head section 12 has a first electrode 14 and a second electrode 15. The block handle 11 has a power source 17 incorporated therein, to supply electric current to the first and second electrodes 14, 15. The oral cavity cleaning tool 10 generates effective chlorine by causing electric current to flow between the first and second electrodes 14, 15 while keeping the first and second electrodes 14, 15 in contact with an oral fluid that includes chloride ions.

The first electrode 14 and the second electrode 15 may be embedded in the outer surface of the head section 12 with a part thereof being exposed. While the first electrode 14 and the second electrode 15 may be formed from, for example, platinum, gold, copper, zinc, tin, stainless steel, carbon or the like, the material is not limited to these and needs only to be electrically conductive. The first and second electrodes 14, 15 may also be made by plating the surface with such an electrically conductive material.

The distance between the first electrode 14 and the second electrode 15, that is the distance of the closest first and second electrodes 14, 15, is preferably in a range from 1 mm to 20 mm, and more preferably from 1 mm to 15 mm. It is not preferable that the distance between the electrodes is less than 1 mm, because the region where effective chlorine is generated is too small to obtain a sufficient amount of effective chlorine that is used in sterilization. It is not preferable that the distance between the electrodes is more than 20 mm, because the region where effective chlorine is generated is too large to generate effective chlorine in a localized fashion. In actuality, effective chlorine is generated by the anode among the pair of electrodes, and diffuses within a certain region around the anode. When the power source 17 supplies direct current, then effective chlorine is generated from only one of the electrodes. When the power source 17 supplies alternate current, effective chlorine is generated alternately from the pair of electrodes.

The block handle 11 is formed from an insulating material, and a switch 16 is provided on the surface thereof. The power source 17 is disposed inside the block handle 11. Incorporated inside the block handle 11 and the head section 12 is a lead wire 19 that connects the first electrode 14 and the second electrode 15, the switch 16, and the power source 17. The power source 17 may be connected with a constant current circuit that prevents surge current from flowing. The power source 17 may also be provided with a timer so as to set the duration of power supply such as 30 seconds, 1 minute or 3 minutes for the reason of safety.

The block handle 11 may be formed from an insulating material such as polystyrene resin (PS), polypropylene resin (PP), polyethylene terephthalate resin (PET), acrylonitrile butadiene styrene resin (ABS), cellulose propionate resin (CP), polyallylate resin, polycarbonate resin, acrylonitrile styrene resin (AS) or the like which may be used individually or in combination. As the block handle 11 is formed from an insulating material, electric current does not flow in the body of a person who uses the oral cavity cleaning tool 10.

The switch 16 is preferably covered with rubber or the like on the control exposed on the surface so as to insulate and protect it from water. Output voltage of the power source 17 may be roughly in a range from 0.1 to 12 V. For example, a button cell having voltage rating in a range from 1.5 to 9 V may be used as the power source. The battery is preferably accommodated in a battery housing so as to be replaceable from the outside. Dry cell, button cell, nickel-cadmium cell, nickel-hydrogen cell, lithium ion cell or the like may be used as the battery. Besides a battery, the power source 17 may also be one that utilizes the potential difference between a semiconductor and a metal, or the so-called solar cell such as photoelectric conversion element. The power source may be provided with a booster and a resistor so as to control the acting voltage to within a range from 1.5 to 9 V. The power source 17 may be, instead of being incorporated in the block handle 11, attached to the block handle 11 from the outside.

As the power source 17 having voltage rating in a range from 1.5 to 9 V is employed, the potential difference between the electrodes 14 and 15 can be set within the range from 1.5 to 9 V. Setting the potential difference within this range enables it to efficiently generate effective chlorine. A potential difference less than 1.5 V is not preferable, since a sufficient amount of effective chlorine cannot be generated in that case. A potential difference higher than 9 V is not preferable, since the user may feel electric shock when the oral cavity cleaning tool 10 is applied to the inside of the oral cavity.

In the case of constant current circuit, the circuit may be constituted with a resistor connected thereto. The resistor may be either a fixed resistor or a variable resistor. In addition, a transistor may be added in order to stabilize the current further. Resistance of the constant current circuit may be, for example, roughly in a range from 750 Ω to 4500 kΩ. This makes it possible to keep the electric current flowing between the first electrode 14 and the second electrode 15 in a range from 20 μA to 3 mA, preferably from 50 μA to 2 mA, even when the resistance between the first electrode 14 and the second electrode 15 varies significantly. This enables it to maintain the rate of generating effective chlorine always constant. Particularly since effective chlorine undergoes substantial degradation with time, the concentration of effective chlorine can be maintained always constant by keeping the rate of generating effective chlorine constant. Stabilizing the electric current also prevents a surge current from entering, thus reducing the electric shock to the user.

When the head section of the oral cavity cleaning tool 10 having the constitution described above is immersed in physiological saline and is supplied with power to flow electric current between the electrodes, chloride ion included in the physiological saline is transformed into effective chlorine. At this time, the concentration of effective chlorine in the physiological saline falls in a range from 2 ppm to 100 ppm, preferably 5 ppm to 60 ppm when power is supplied for 3 minutes for 2 ml of physiological saline. When the concentration of effective chlorine is within the range described above, efficient sterilization can be achieved without causing harm to the human body, even when the oral cavity cleaning tool is used in the oral cavity. It is not preferable that the concentration of effective chlorine is lower than 2 ppm, because sufficient effect of sterilization cannot be achieved when used in the oral cavity. It is not preferable that the concentration of effective chlorine is higher than 100 ppm, because mucous tissue in the oral cavity may be harmed when the tool is used in the oral cavity.

When the oral cavity cleaning tool 10 having the constitution described above is immersed in physiological saline and is supplied with power (0.1 to 12 V) to flow electriccurrent between the electrodes, rate of generating effective chlorine is in a range from 0.5 ppm per minute to 35 ppm per minute, preferably from 1.5 ppm per minute to 20 ppm per minute. A rate of generating effective chlorine lower than 0.5 ppm per minute is not preferable, since the rate of decomposition exceeds the rate of generating effective chlorine and the concentration of effective chlorine in the oral cavity becomes lower in that case. A rate of generating effective chlorine higher than 35 ppm per minute is not preferable, since the rate of generating effective chlorine far exceeds the rate of decomposition and the concentration of effective chlorine in the oral cavity becomes too high in that case.

When the oral cavity cleaning tool 10 having the constitution described above is used in the oral cavity, effective chlorine can be generated through electrolysis by using chloride ion contained in the oral cavity, thus making it possible to efficiently use the effective chlorine for sterilization in the oral cavity. Also because electric circuit is completed by establishing continuity between the first electrode 14 and the second electrode 15 so that the electric current flows only in the oral cavity, not through an arm, the oral cavity cleaning tool having satisfactory sterilization power can be made without being influenced by the resistance of the human body that varies significantly depending on the physique of the body, sex and age.

Figure 2:
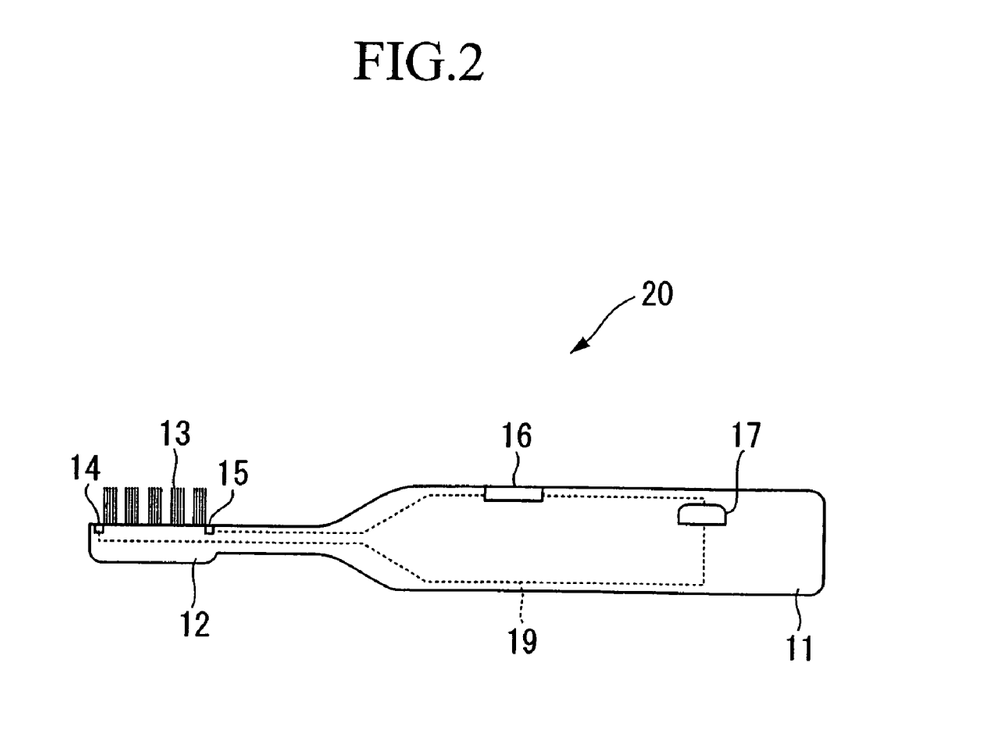
FIG. 2 shows an example of applying the oral cavity cleaning tool to a toothbrush.
Figure 3:
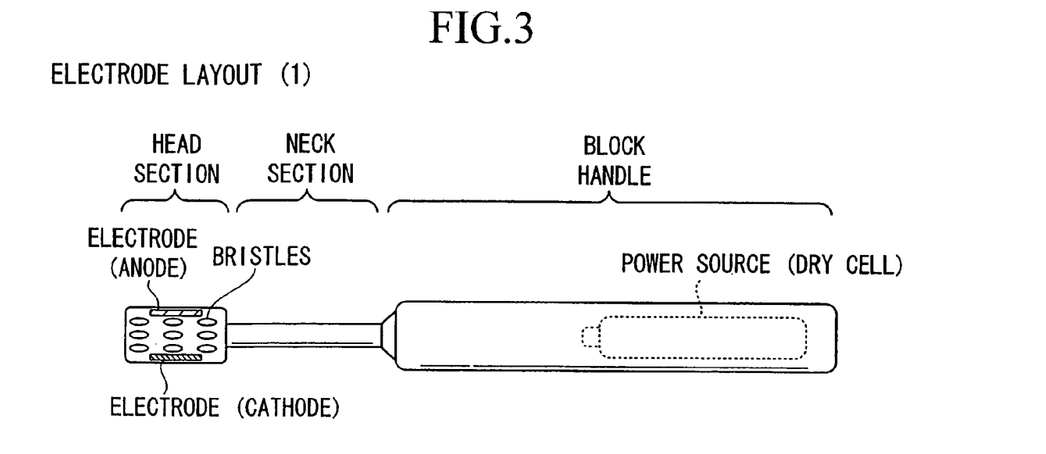
FIGS. 3 through 7 are diagrams showing examples of electrode layout of the oral cavity cleaning tool.
Figure 4:
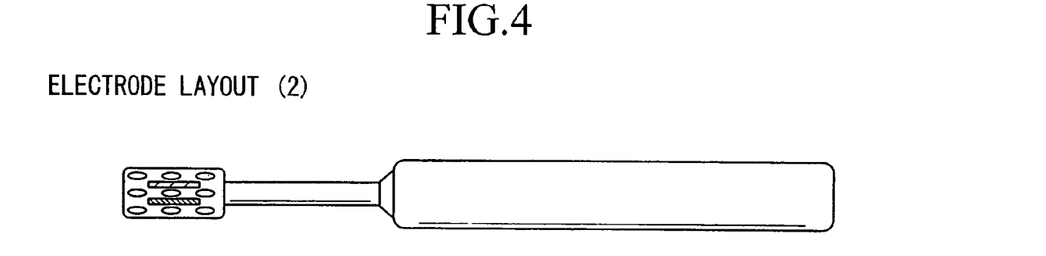
Figure 5:
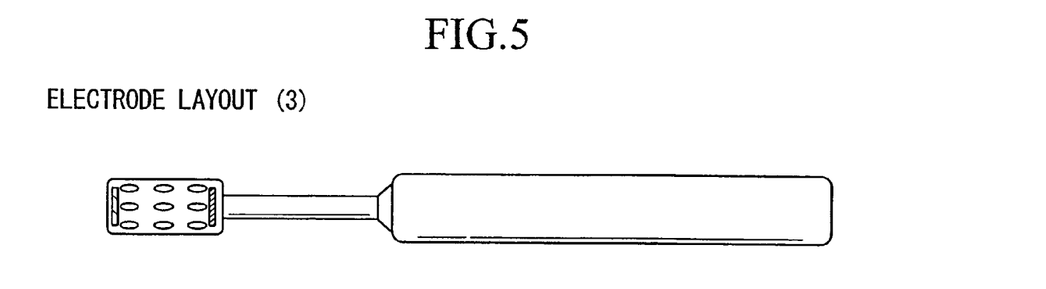
Figure 6:
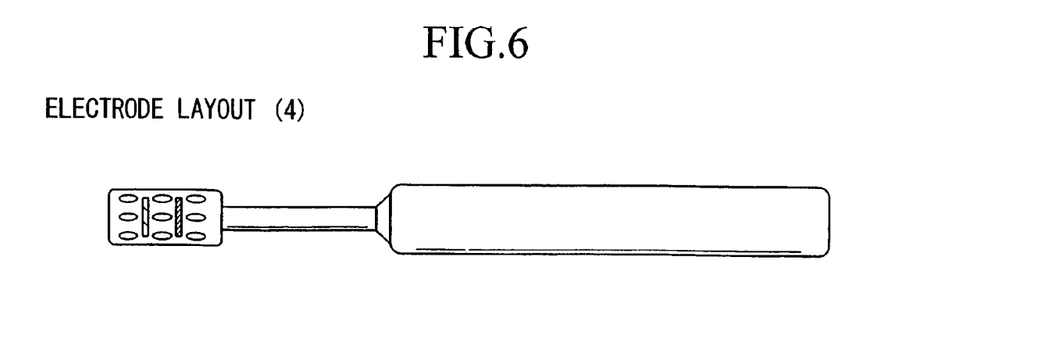
Figure 7:
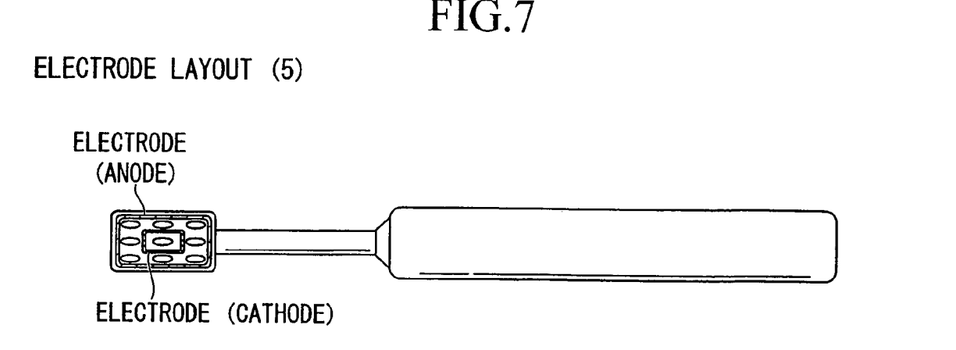

The oral cavity cleaning tool of the present invention may have brushing bristles planted in the head section as shown in FIG. 2.

The oral cavity cleaning tool 20 shown in FIG. 2 has brushing bristles 13 planted in the head section 12.

The brushing bristles 13 perform the function of a toothbrush to efficiently remove dental plaque.

The brushing bristles 13 may be formed from, for example, a polyester resin such as polymethylene terephthalate (PTT), polybutylene terephthalate (PBT) or polyethylene terephthalate (PET), a polyamide such as nylon 6, nylon 66, nylon 6-10, nylon 6-12 or nylon 12, polyolefin such as polyethylene or polypropylene, or vinyl polyhalide such as polyvinylidene fluoride, that can be applied to melt spinning.

The brushing bristles may also be formed from a mixture of two or more of these resins, or from a natural material such as the hair of pig or goat.

Moreover, electrically conductive bristles may also be used. When electrically conductive bristles are used as the brushing bristles 13, the first electrode 14 and the second electrode 15 may be embedded in the head section 12 while the electrically conductive bristles are put into contact with the first electrode 14 and the second electrode 15.

The oral cavity cleaning tool of the present invention may have the electrodes disposed in the layouts shown in FIGS. 3 through 7.

Figure 8:
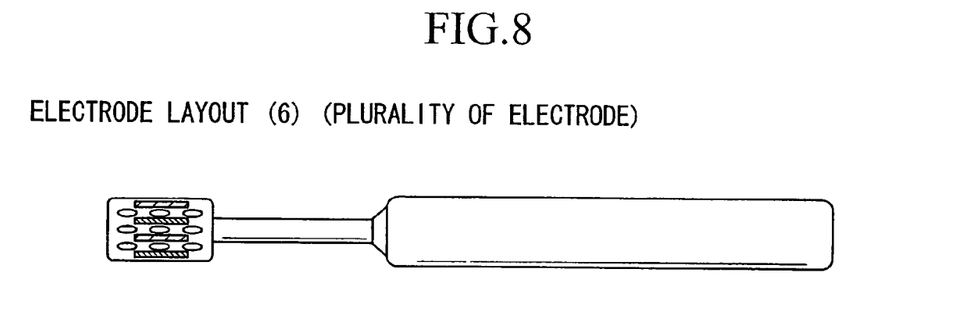
FIGS. 8 through 9 are diagrams showing examples of electrode layout of the oral cavity cleaning tool having plurality of electrodes.
Figure 9:
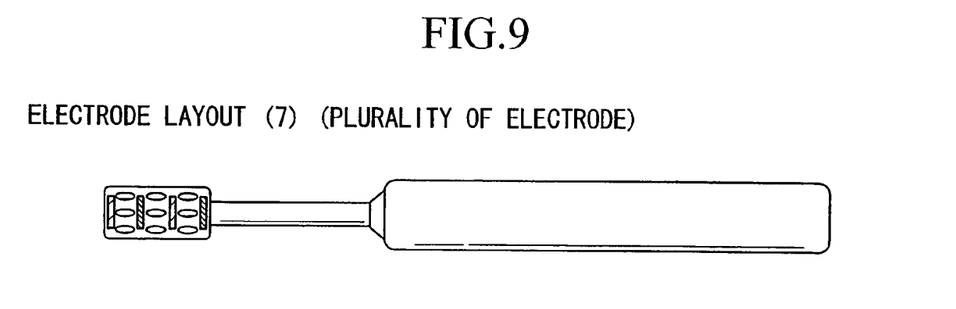

The oral cavity cleaning tool of the present invention may also have a plurality of electrodes disposed in the layouts shown in FIG. 8 and FIG. 9.

Figure 10:
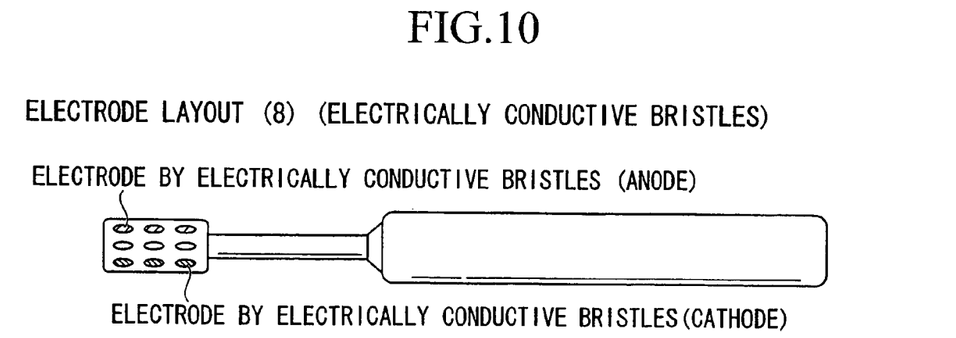
FIGS. 10 and 11 are diagrams showing examples of electrode layout of the oral cavity cleaning tool having electrically conductive bristles.
Figure 11:
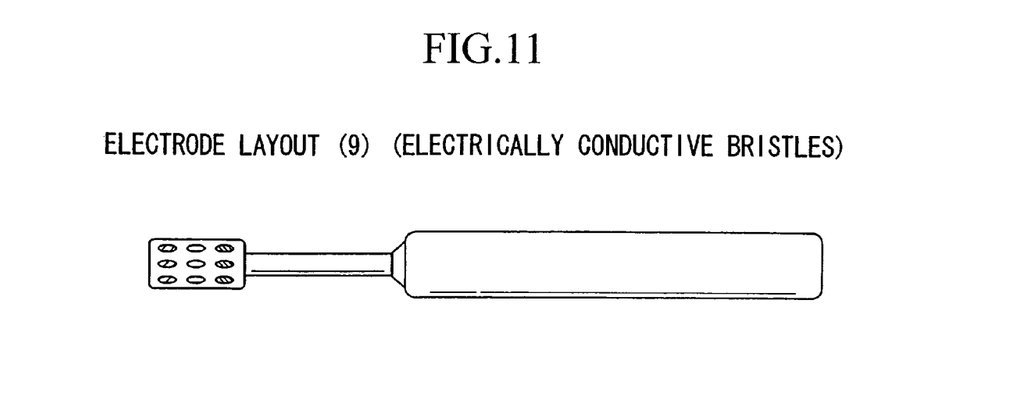
Figure 12:
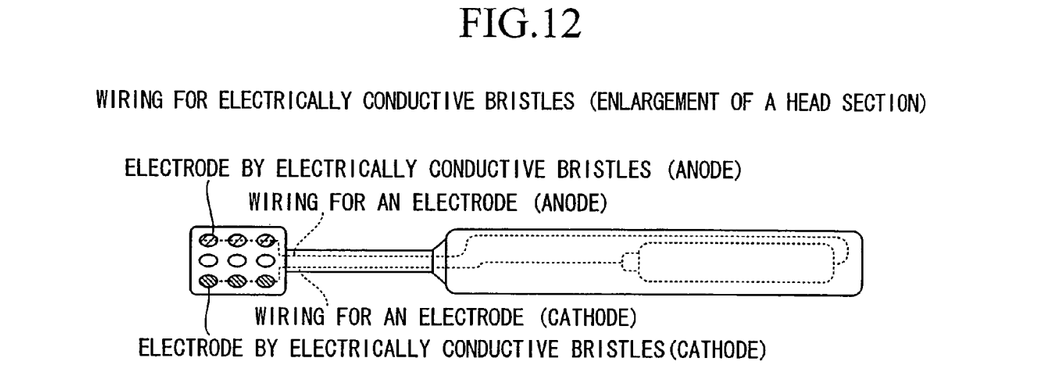
FIG. 12 is a diagram showing an example of wiring for electrodes of the oral cavity cleaning tool having electrically conductive bristles.
Figure 13:
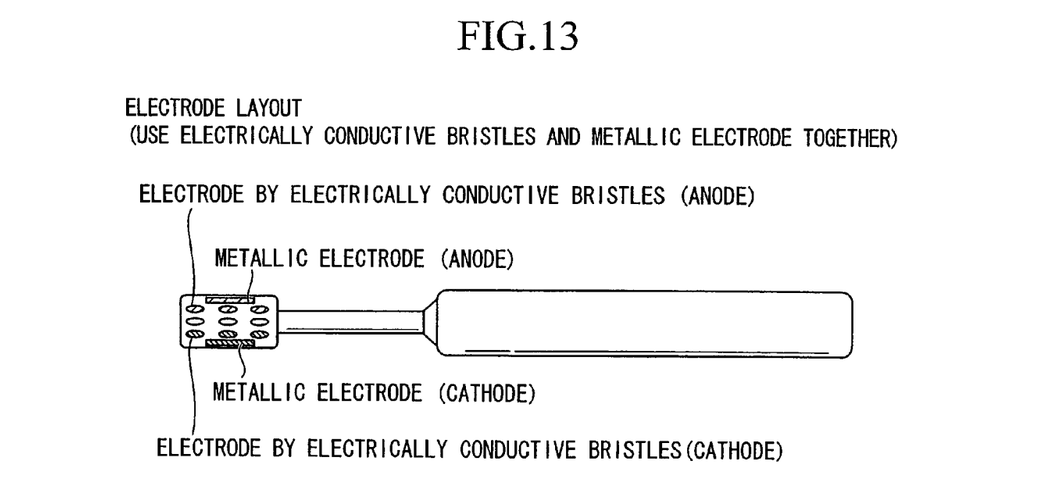
FIG. 13 is a diagram showing an example of electrode layout of the oral cavity cleaning tool that uses electrically conductive bristles and metallic electrode together.

When the electrically conductive bristles are used, the electrodes may be disposed as shown in FIG. 10 and FIG. 11. When the electrodes are disposed as shown in FIG. 10, they may be wired as shown in FIG. 12. The oral cavity cleaning tool of the present invention may also employ the electrically conductive bristles and metallic electrode in combination as shown in FIG. 13.

EXAMPLES

Experiment 1

The present applicant verified the characteristics of the oral cavity cleaning tool of the present invention, with the oral cavity cleaning tool of the present invention shown in FIG. 1 being prepared. The first electrode and the second electrode were made of platinum, and were disposed at a space selected within a range from 0 mm to 20 mm from each other. The block handle was made of polypropylene resin (PP). Power was supplied from a button cell with voltage of 3 V or 4.5 V. Oral fluid shown in the table was used.

Sterilization effect was verified using the oral cavity cleaning tool described above, by evaluating the effect of sterilizing the oral bacteria S. mutans. Sterilized physiological saline was used as the oral fluid to control the concentration of the oral bacteria to $10^6$ cfu/ml. 2 ml of the liquid with the controlled concentration of bacteria was transferred to a multi-well plate, and the oral cavity cleaning tool was applied thereto and electric current was caused to flow for 3 minutes, with the concentration of the bacteria after flowing the current measured. The concentration of effective chlorine in the physiological saline after immersion was measured by means of SIBATA simplified measurement kit and absorption spectrophotometry. Table 1 shows the results of measuring the concentration of effective chlorine after flowing electric current of different magnitudes and the sterilization power. Table 2 shows the results of measuring the concentration of effective chlorine and the sterilization power while changing the oral fluid among 0.9% salt water, 0.45% salt water and an artificial saliva (Saliveht, manufactured by Teijin Pharma Limited). City water was used for comparison. Results shown in Table 2 were obtained by setting the distance between the electrodes to 5 mm and the voltage to 3 V.

Rating of the sterilization power shown in Tables 1 and 2 is indicated as A when the concentration of bacteria decreased from $10^6$ cfu/ml to $10^3$ cfu/ml, B when the concentration of bacteria decreased from $10^6$ cfu/ml to $10^4$ cfu/ml, C when the concentration of bacteria decreased from $10^6$ cfu/ml to $10^5$ cfu/ml, and D when the concentration did not change.

TABLE 1

|  | No. 1 | No. 2 | No. 3 | No. 4 |
| --- | --- | --- | --- | --- |
| Distance between electrodes (mm) | 0 | 1 | 10 | 10 |
| Voltage | 3 V | 4.5 V | 3 V | 9 V |
| Concentration of effective chlorine (ppm) | Not detected | 60 | 20 | 100 |
| Sterilization power | D | A | A | A |

TABLE 2

|  | 0.9% Salt water | 0.45% Salt water | Artificial saliva | City water |
| --- | --- | --- | --- | --- |
| Concentration of effective chlorine (ppm) | 20 | 10 | 5 | Not detected |
| Sterilization power | A | A | B | D |

Tables 1 and 2 show that sterilization effect was obtained when the concentration of effective chlorine was in a range from 2 ppm to 100 ppm. Fairly high effect of sterilization was obtained when the concentration of effective chlorine was 5 ppm or higher. When the concentration of effective chlorine was 70 ppm or higher, odor of chlorine was felt a little. Distinct odor of chlorine was felt when the concentration was 100 ppm. Thus it was found that concentration of effective chlorine is preferably in a range from 5 ppm to 60 ppm.

Experiment 2

Value in use of a toothbrush, to which the oral cavity cleaning tool of the present invention was applied, was evaluated. The toothbrush according to the present invention shown in FIG. 2 was prepared. The toothbrush has the same constitution as that of No. 3 in Experiment 1, except for planting brushing bristles in the head section. The first electrode and the second electrode were made of platinum, and were disposed at a space of 10 mm and 15 mm from each other. The block handle was made of polypropylene resin (PP). Power was supplied from a button cell with voltage of 3 V. The toothbrush of No. 3 with the power switch turned off was used as a comparative example (No. 1).

Value in use of the toothbrushes was evaluated by 30 panelists. The panelists' evaluation of the value in use upon brushing teeth for 3 minutes is shown in Table 3. Result of free answer evaluation is shown in Table 4. In Table 3, A shows evaluation of excellent, B shows good, C shows inability to decide good or bad, and D shows bad.

TABLE 3

|  | No. 3 | No. 1 |
| --- | --- | --- |
| Distance between electrodes (mm) | 10 | 10 |
| Voltage (V) | 3 | 0 |
| Summarized evaluation | A | D |

TABLE 4

| | Free answer evaluation |
|---|---|
| No. 3 | Smooth, refreshed |
| No. 1 | Not impressed |

As shown in Table 3, the toothbrush No. 3 was highly evaluated in the summarized evaluation, and rated as high in freshness and smoothness in the oral cavity after use in the free answer evaluation as shown in Table 4. Thus excellent characteristic was demonstrated in use by the toothbrush of the present invention that generates effective chlorine.

Experiment 3

Comparison with Commercialized Toothbrush

Generation of effective chlorine was evaluated using commercialized toothbrushes.

PM Brush and Soladey (both brand names) were used as the commercialized toothbrush. The PM Brush has two different metals embedded in the head section. Accordingly, the head section of the PM Brush was cut off and the rest of it was placed vertically at the bottom of a test tube having capacity of 15 ml over which 2 ml of physiological saline was poured. It was confirmed that the metallic members were completely submerged in the physiological saline. After leaving the sample to stand still in the physiological saline for 3 minutes, concentration of effective chlorine in 2 ml of physiological saline was measured, using SIBATA weak acidity electrolytic water kit.

Soladey is activated when the semiconductor provided in the neck section is wetted with water. Accordingly, the plug-in head section was removed and the neck section of the semiconductor was placed vertically in a test tube having capacity of 15 ml over which 2 ml of physiological saline was poured in the same way as PM Brush. After leaving the sample to stand still in the physiological saline for 3 minutes, the concentration of effective chlorine in the physiological saline was measured, using SIBATA weak acidity electrolytic water kit.

For comparison, the toothbrush according to Example 1 of the present invention was used with voltage of 3 V and distance of 10 mm between the electrodes. The head section provided with the electrodes placed in a test tube having capacity of 15 ml and was supplied with power for 3 minutes. Then concentration of effective chlorine in 2 ml of physiological saline was measured, using SIBATA weak acidity electrolytic water kit.

The results are shown in Table 5.

TABLE 5

| Toothbrush tested | Concentration of effective chlorine |
|---|---|
| PM Brush | Not detected |
| Soladay | Not detected |
| Example 1 | 20 ppm |

Experiment 4

A toothbrush similar to that used in Experiment 1 was used with voltage and distance between the electrodes being set as shown in Table 6. The rate of generating effective chlorine per unit time was measured by means of SIBATA simplified measurement kit or absorption spectrophotometry, and investigated the sterilization power and irritation to the oral mucous.

The experiment was conducted similarly to Experiment 1, using *S. mutans*. Irritation to the oral mucous was evaluated by whether 10 panelists had uneasy feeling or not. The results are shown in Table 6.

TABLE 6

| Rate of generating effective chlorine (ppm/min.) | | 1.7 | 6.7 | 10 | 20 | 33.3 | 36.7 |
|---|---|---|---|---|---|---|---|
| Energization conditions | Voltage (V) | 3 | 3 | 3 | 3 | 4.5 | 4.5 |
| | Distance between electrodes (mm) | 5 | 10 | 5 | 5 | 2 | 1 |
| Sterilization power | | B | A | A | A | A | A |
| Irritation to oral mucous | | none | none | none | none | none | felt |

Table 6 shows that sterilization power varies depending on the rate of generating effective chlorine. Change in the concentration of effective chlorine with time was measured, and decreasing trend of the concentration was verified as shown in Table 7. The concentration decreased by 5 ppm in 10 minutes, showing a decreasing rate of 0.5 ppm per minute. It is not preferable that the rate of generating effective chlorine was lower than 0.5 ppm per minute, because the rate of decomposition exceeded the rate of generating effective chlorine and sufficient amount of effective chlorine could not be obtained. It was found that the rate of generating effective chlorine is preferably 5 ppm per minute or higher.

As shown in Table 6, no significant influence on the oral mucous was recognized when the rate of generating effective chlorine was 33.3 ppm per minute, but brushing the teeth for 3 minutes while the rate of generating effective chlorine was 36.67 ppm per minute resulted in irritation feeling. This was probably because the rate of generating effective chlorine was far higher than the rate of decomposition, resulting in a concentration of effective chlorine that was too high.

Thus it has been found that the rate of generating effective chlorine is preferably in a range from 0.5 ppm per minute to 35 ppm per minute, more preferably from 1.67 ppm per minute to 20 ppm per minute.

TABLE 7

| | Time lapsed | | | |
|---|---|---|---|---|
| | 0 min. | 3 min. | 5 min. | 10 min. |
| Concentration of effective chlorine | 30 ppm | 28-29 ppm | 27-28 ppm | 25 ppm |

INDUSTRIAL APPLICABILITY

The oral cavity cleaning tool of the present invention generates effective chlorine from chloride ions that are present in the oral cavity through electrolysis, so that the effective chlorine can be immediately used for sterilization efficiently without allowing the degradation of effective chlorine.

What is claimed is:
1. An oral cavity cleaning tool comprising:
a block handle;
a head section including brushing bristles, said head section extending from said block handle;

at least a pair of electrodes provided on said head section, said electrodes being embedded in an outer surface of said head section and a distance between said electrodes being in a range of 1 mm to 20 mm;

a power source that supplies electric current to said electrodes by keeping them at different potentials such that current flowing between said electrodes transforms chloride ions in an oral fluid into effective chlorine when placed into contact with the oral fluid; and a constant current circuit connected with said power source, said constant current circuit maintaining a rate of current sufficient to keep constant the generation of the effective chlorine, a resistance of said constant current circuit being in a range from 750 Ω to 4500 kΩ and said current between said electrodes being in a range from 50 μA to 2 mA.

2. The oral cavity cleaning tool according to claim 1, wherein said brushing bristles are electrically conductive bristles.

3. The oral cavity cleaning tool according to claim 1, wherein said constant current circuit provides current sufficient to generate a concentration of effective chlorine that is in a range from 2 ppm to 100 ppm when said oral fluid is physiological saline.

4. The oral cavity cleaning tool according to claim 1, wherein said constant current circuit provides current sufficient to cause the rate of generation of effective chlorine to be in a range from 0.5 ppm per minute to 35 ppm per minute when said oral fluid is physiological saline.

* * * * *